(12) United States Patent
Karst et al.

(10) Patent No.: US 9,517,353 B2
(45) Date of Patent: Dec. 13, 2016

(54) PHOTOVOLTAIC GENERATION DEVICE AND SYSTEM AND APPLICATION THEREOF TO AN IMPLANTABLE MEDICAL DEVICE

(71) Applicant: COMMISSARIAT A L'ENERGIE ATOMIQUE ET AUX ENERGIES ALTERNATIVES, Paris (FR)

(72) Inventors: Nicolas Karst, Folkling (FR); Simon Perraud, Bandol (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/770,227

(22) PCT Filed: Feb. 20, 2014

(86) PCT No.: PCT/IB2014/059128
§ 371 (c)(1),
(2) Date: Nov. 24, 2015

(87) PCT Pub. No.: WO2014/128642
PCT Pub. Date: Aug. 28, 2014

(65) Prior Publication Data
US 2016/0082272 A1    Mar. 24, 2016

(30) Foreign Application Priority Data

Feb. 25, 2013  (FR) ...................................... 13 51640

(51) Int. Cl.
*A61N 1/00*     (2006.01)
*A61N 1/378*    (2006.01)
(Continued)

(52) U.S. Cl.
CPC .......... *A61N 1/3787* (2013.01); *H01L 25/167* (2013.01); *H01L 31/0322* (2013.01); *H01L 31/12* (2013.01);
(Continued)

(58) Field of Classification Search
CPC .... H01L 25/167; H01L 31/0322; H01L 31/12; A61N 1/3787; H02J 7/35; Y02E 10/541
See application file for complete search history.

(56) References Cited

U.S. PATENT DOCUMENTS

2006/0085051 A1    4/2006  Fritsch
2011/0134293 A1*   6/2011  Tanaka ..................... G02B 7/34
                                                        348/280

FOREIGN PATENT DOCUMENTS

DE      44 35 602 A1      4/1996
WO    WO 2012/104503 A1   8/2012

OTHER PUBLICATIONS

International Search Report and Written Opinion for corresponding International Application No. PCT/IB2014/059128, dated Jul. 31, 2014.
(Continued)

*Primary Examiner* — George Manuel
(74) *Attorney, Agent, or Firm* — Alston & Bird LLP

(57) ABSTRACT

A photovoltaic device including a CIGS photovoltaic module having a so-called top surface, intended to be exposed to light radiation; and a light emitting diode emitting light at a wavelength of less than 600 nm and transparent to radiation in the near infrared, attached to the top surface of the photovoltaic module. A photovoltaic generation system having: at least one such photovoltaic device; a system of switches to selectively connect the photovoltaic module to the light emitting diode or to a terminal supplying an external load; and a control circuit for controlling the system of switches. An electrical system having: such a photovol-
(Continued)

taic generation system; a battery connected to the supply terminal; and at least one electronic circuit connected to the battery in order to be powered. An implantable medical device having such an electronic system.

13 Claims, 1 Drawing Sheet

(51) Int. Cl.
*H01L 25/16* (2006.01)
*H01L 31/032* (2006.01)
*H01L 31/12* (2006.01)
*H02J 7/35* (2006.01)

(52) U.S. Cl.
CPC .......... *H02J 7/35* (2013.01); *H01L 2924/0002* (2013.01); *Y02E 10/541* (2013.01)

(56) References Cited

OTHER PUBLICATIONS

Pudov, A. O. et al., *CIGS J-V distortion in the absence of blue photons*, Thin Solid Films, vol. 480-481, (Jun. 1, 2005) 273-278.

K. Murakawa et al., *A wireless near-infrared energy system for medical implants* IEEE Engineering Medicine Biology 18, 70 (1999).

K. Nakahara et al., *Improved External Efficiency InGaN-Based Light-Emitting Diodes with Transparent Conductive Ga-Doped ZnO as p-Electrodes*, Japanese Journal of Applied Physics, vol. 43, No. 2A, 2004, pp. L 180-L 182.

* cited by examiner

PHOTOVOLTAIC GENERATION DEVICE AND SYSTEM AND APPLICATION THEREOF TO AN IMPLANTABLE MEDICAL DEVICE

FIELD

The invention relates to a photovoltaic generation device and system that are particularly suitable for implanted biomedical device applications, and in which the illumination is carried out transcutaneously. The invention also relates to an electronic system comprising such a photovoltaic generation system and to an implantable medical device comprising such an electronic system.

A generating device and system and an electronic system according to the invention may also be used in applications other than implantable medical device applications.

BACKGROUND

In the last few years an increasing interest in implantable medical devices, such as cardiac stimulators, neurostimulators or systems enabling in vivo biomedical detection and control, has been observed. In the near future, implantable sensors will for example allow early diagnosis of certain diseases or allow the blood sugar or oxygen level to be precisely monitored in real time. However, in order to function autonomously, implantable medical devices require an internal power supply generally provided by a primary battery. Batteries, the energy densities of which are relatively high (as high as 300 Wh/l) allow small systems to be powered over a duration ranging from a few days to a few years depending on the required power. Thus, for implantable medical devices, the power densities of the highest-performance batteries currently available oblige the latter to be regularly replaced. However, for in vivo applications, the replacement of batteries is not a trivial matter because it requires a surgical intervention.

In order to avoid the replacement of primary batteries, it has been proposed to use what are called "secondary" batteries, recharged by way of an energy-harvesting device such as a coil (recharging by electromagnetic induction), an ultrasonic transducer (recharging by ultrasound) or alternatively a photovoltaic cell (recharging by near-infrared light). This type of device has the advantage of not requiring surgical interventions to replace discharged batteries. Specifically, provided the secondary batteries are periodically recharged by way of the aforementioned energy-harvesting devices, the lifetime of this type of device may approach that of the patient.

Photovoltaic recharging is a particularly promising approach, but one that is confronted with considerable technical difficulties.

In their article of 1999 "*A wireless near-infrared energy system for medical implants*" IEEE Engineering Medicine Biology 18, 70 (1999), K. Murakawa et al. proposed to use a near-infrared laser coupled to a photovoltaic cell made of silicon to power a secondary battery. It is a question of implanting the photovoltaic cell and the battery under the skin and illuminating the photovoltaic cell by way of the near-infrared laser, located outside the body, when the battery must be recharged. Specifically, the low absorption of near-infrared radiation (780-1400 nm) by biological tissues makes it possible for the radiation to reach the implanted photovoltaic cell. However, photovoltaic cells made of silicon have a relatively large thickness of about 100 μm, thereby making them stiff and therefore not very suitable for subcutaneous implantation. Thin-film photovoltaic cells, the thickness of which may be as small as 10 μm, and which may be produced on flexible substrates, are a more promising alternative. Among the various types of thin-film photovoltaic cells, those referred to as "CIGS" cells (CIGS is the acronym of copper-indium-gallium-selenium, these cells comprising an absorbing layer made of an alloy of general formula $CuIn_{1-x}Ga_x(Se_{1-y}S_y)_2$, where $0<x<1$, $0 \leq y \leq 1$) are of particular interest because of their high efficiency—comparable to that of cells made of silicon and this for clearly much lower thicknesses.

However, CIGS cells have a characteristic that proves to be a major drawback in uses implementing transcutaneous illumination. Specifically, it has been demonstrated that such cells can achieve an optimal electrical performance only if the radiation illuminating them contains photons of energy higher than the width of the bandgap of their buffer layer. See in this regard the article by A. Pudov et al., "CIGS J-V distortion in the absence of blue photons", Thin Solid Films 480 (2005), 273-278. Specifically, if the energy of the photons is higher than the width of the bandgap of the buffer layer, some of the photons are absorbed by the buffer layer creating electron-hole pairs, the photogenerated holes making it possible to neutralize acceptor type defects located on the surface of the absorber, thus decreasing the barrier to photoelectrons and enabling a more advantageous alignment of the bands.

Conventionally, the buffer layers used in this type of device are compounds based on zinc $[ZnO_{1-x}S_x]$, cadmium (CdS) or indium ($In_2S_3$), the bandgap widths of which are 3.7 eV, 2.8 eV and 2.4 eV, respectively. Thus, it is necessary to illuminate cells having a buffer layer made of $Zn(O_{1-x}S_x)$, $In_2S_3$ and CdS with photons of wavelength shorter than 335 nm (ultraviolet), 443 nm (blue) and 516 nm (green), respectively. Even though at wavelengths in the green the transmission of biological tissues is higher than at wavelengths in the blue or ultraviolet, the use of buffer layers based on Cd is not envisionable in implanted biomedical applications because of the very high toxicity of Cd.

It is therefore difficult to envision employing CIGS photovoltaic cells in implantable applications, since the photons in the ultra-violet or the blue that are necessary for the proper operation of these cells are absorbed by biological tissues.

SUMMARY

The invention is aimed at overcoming this difficulty and in allowing the use of photovoltaic cells of "CIGS" type in implantable applications or more generally in the presence of an illumination devoid of photons of sufficiently high energy.

The inventors proceeded from the observation that, to obtain optimal CIGS photovoltaic cell operation, it is not necessary for the flux of photons of energy higher than the bandgap width of the buffer layer to be continuous. Once the acceptor type defects have been neutralized, the cells maintain, for a duration of possibly as much as a few days, a high conversion efficiency even if they are subjected only to illumination comprising only photons of lower energy.

The solution provided by the present invention consists in using a light-emitting diode emitting in the green, blue or ultraviolet, said diode being transparent to longer wavelengths and coupled to a CIGS cell or to a stack of such cells. The CIGS cells, which are illuminated in the red/infrared through the light-emitting diode, generate, with a low efficiency, electrical power that powers the diode. In turn, the "high-energy" radiation of the diode gradually improves the efficiency of the cells; when this efficiency reaches a level considered to be satisfactory, the diode is disconnected and the electrical power generated by the photovoltaic effect is used to power an exterior load, for example to recharge a battery.

Thus, one subject of the invention is a photovoltaic device comprising a CIGS photovoltaic module having a surface, called the upper surface, intended to be exposed to luminous radiation; and a light-emitting diode having a luminous emission at a wavelength shorter than or equal to 600 nm, preferably shorter than or equal to 443 nm and even more preferably comprised between 250 and 400 nm, and transparent to radiation in the near infrared, fastened to said upper surface of the photovoltaic module.

According to various embodiments of such a device:
Said light-emitting diode may have a luminous emission at a wavelength corresponding to a photonic energy higher than a bandgap width of a buffer layer of said photovoltaic module.

Said CIGS photovoltaic module may be suitable for generating an electrical current when its upper surface is illuminated by near infrared radiation to which said light-emitting diode is transparent.

Said photovoltaic module may comprise a plurality of photovoltaic cells connected in series. In particular, said photovoltaic cells connected in series may be produced in the form of a thin-film stack deposited on a common substrate.

Another subject of the invention is a photovoltaic generation system comprising a CIGS photovoltaic module having a surface, called the upper surface, intended to be exposed to luminous radiation; and a light-emitting diode having a luminous emission at a wavelength shorter than 600 nm, preferably shorter than or equal to 443 nm and even more preferably comprised between 250 and 400 nm, and transparent to radiation in the near infrared, arranged so as to be able to illuminate said photovoltaic module; a system of switches for selectively connecting said photovoltaic module to said light-emitting diode or to a supply terminal of an exterior load; and a control circuit for controlling said system of switches.

Advantageously, said photovoltaic module and said light-emitting diode may form a photovoltaic device such as described above.

Said control circuit may be suitable for measuring an electrical power generated by said photovoltaic module and controlling said switching system depending on the measured power. In particular, said control circuit may be suitable for controlling said switching system such that said photovoltaic module powers said light-emitting diode when said measured power is below a preset threshold, then powers an exterior load connected to said supply terminal.

Yet another subject of the invention is an electronic system comprising a photovoltaic generation system such as described above, a battery connected to said supply terminal so as to be recharged by said photovoltaic generation system and at least one electronic circuit connected to said battery so as to be powered.

Yet another subject of the invention is an implantable medical device comprising such an electronic system. In this case, the electronic circuit may especially be a generator of stimulating pulses; a circuit for detecting, acquiring, processing and/or transmitting signals acquired by an implanted sensor or else a control circuit controlling an implanted device for delivering medication.

BRIEF DESCRIPTION OF THE DRAWINGS

Other features, details and advantages of the invention will become apparent on reading the description, which is given with reference to the appended drawings, which are provided by way of example and show, respectively.

DETAILED DESCRIPTION

Figure 1:
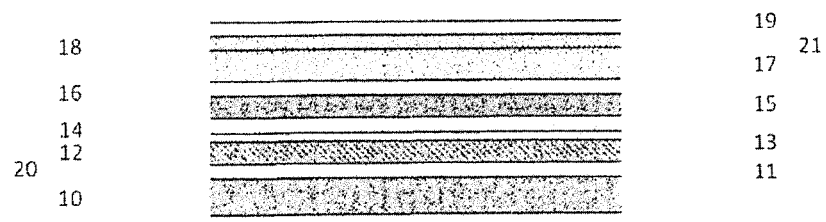
FIG. 1, a schematic cross-sectional representation of a photovoltaic device according to one embodiment of the invention.

In FIG. 1, the reference 10 indicates a flexible or stiff substrate, which may especially be made of soda-lime glass, a polymer or a metal (steel, aluminum, titanium, etc.). On the substrate 10, of thickness comprised between 10 μm and 5 mm and preferably comprised between 0.5 mm and 2 mm and for example of about 1 mm, is deposited an electrode 11 made of molybdenum (Mo) the thickness of which is comprised between 100 nm and 2 μm and preferably between 200 nm and 1 μm and for example of about 500 nm. A p-type semiconductor CIGS [Cu(In$_{1-x}$Ga$_x$) (Se$_{1-y}$S$_y$)$_2$, where 0<x<1, 0≤y≤1] layer 12, serving as a light absorber, is deposited on the electrode 11 by vacuum coevaporation of elementary materials (Cu, In, Ga, Se) or by selenization annealing of metal precursors deposited beforehand. The stoichiometric coefficients x and y may be very variable; specifically, efficiencies higher than 19% have been obtained with 0.69≤Cu/(In+Ga)≤0.98 and 0.21≤Ga/(In+Ga)≤0.38.

In order to produce a pn junction, an n-type semiconductor "buffer" layer 13 of ZnO$_{1-x}$S$_x$ or InO$_{1-x}$S$_x$ (0<x<1) of a thickness comprised between 10 and 100 nm and preferably of 50 nm is deposited by chemical bath, atomic layer deposition (ALD), physical vapor deposition (CVD), etc. on the CIGS layer 12. Next, a layer 14 of a transparent conductive oxide is deposited on the layer 13 in order to form a transparent electrode. It may especially be a layer of ZnO doped with Al to 2% by weight, having a thickness of about 500 nm. It may equally be a layer of indium tin oxide (ITO) or of SnO$_2$. Thus, a photovoltaic cell is obtained, indicated in FIG. 1 by the reference 20. In fact, it is generally preferable to repeat a plurality of times the stack of layers 11-12-13 in order to produce a photovoltaic module (reference 22 in FIG. 3) formed by series connection of elementary cells. This makes it possible to generate a higher voltage, able to be used directly to power the light-emitting diode. Thus, series connection of 10 cells of voltage comprised between 0.5 V-0.6 V (typical voltage at the maximum power point of CIGS cells) may allow voltages of about 5-6 V to be obtained. The current density will depend on the area of the cells making up the photovoltaic module and will possibly range from 30 mA for cells of 1 cm$^2$ to 300 mA for cells of 10 cm$^2$.

The light-emitting diode (LED), indicated by the reference 21, may be fabricated in the following way. A thin film 17 of a p-type semiconductor material is deposited on a substrate 18 of an n-type semiconductor material. For example, a thin film 17 of p-type is deposited by molecular beam epitaxy (MBE) or metal-organic chemical vapor deposition (MOCVD) on a substrate 18 of n-type single-crystal GaN. This type of LED emits in the blue or ultraviolet. Other semiconductor layers may be added to the stack forming the LED 21 in order to improve its emission properties as explained in the article by K. Nakahara et al. "Improved External Efficiency InGaN-Based Light-Emitting Diodes with Transparent Conductive Ga-Doped ZnO as p-Electrodes" Japanese Journal of Applied Physics, Vol. 43, No. 2A, 2004, pp. L 180-L 182.

The n-side electrical contact (reference 19) may be a pad, a metal grid (for example a Ti/Al/Ti/Au stack) or even a layer of a transparent conductor such as ITO. The p-side electrical contact (reference 16) is a transparent electrode that may be a thin film of a transparent conductive oxide based on Ga-doped ZnO (ZnO:Ga), or indeed an ultra-thin metal film (of Au, Cr, etc.) of thickness comprised between 5 and 20 nm. This electrical contact 16 may be complemented by a pad or a metal grid (for example a Ti/Au stack). The LED 21 described here is transparent to near-infrared radiation (780-1400 nm).

The LED 21 may also be fabricated on a flexible substrate, for example by depositing thin organic semiconductor films on a polymer substrate, or by techniques for transferring thin inorganic semiconductor films to polymer substrates.

The complete device, identified by the reference 2, is obtained by fastening the LED 21 on top of the photovoltaic cell 20, i.e. to its "upper" surface, which is opposite the substrate 10 and intended to be illuminated. The LED 21 and the photovoltaic cell 20 may for example be fastened by way of a transparent insulating film 15 possibly consisting of an epoxy resin. The film 15, generally of a thickness comprised between 50 nm and 10 µm, ensures the transparent conductive oxide 14 and the transparent electrode 16 are electrically insulated from each other, and physically separates the photovoltaic cell 20 and the LED 21.

In another embodiment, the photovoltaic cell and the LED have a common transparent electrode 31, thereby making it possible to omit the layer 15. This embodiment is shown in FIG. 2.

Figure 3:
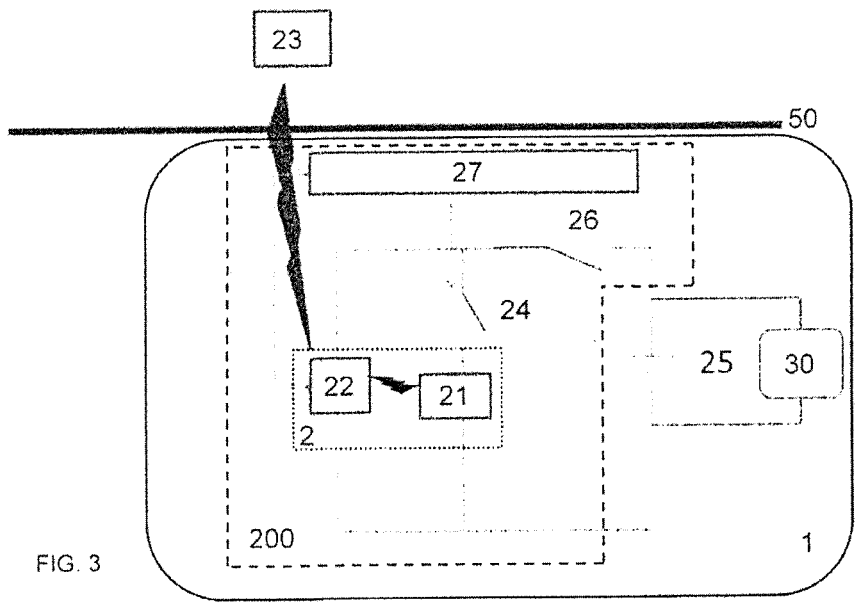
FIG. 3, a functional diagram of an implantable medical device according to another embodiment of the invention.

FIG. 3 shows a functional diagram of an implantable medical device 1 comprising a photovoltaic generation system 200 based on a photovoltaic device 2 such as described above.

As illustrated in this figure, the photovoltaic generation system 200 uses the light energy generated by an external source 23 of radiation, emitting mainly in the near infrared, and transmitted through the skin 50 to charge a battery 25 (for example, a solid-state thin-film microbattery) that in turn powers an electronic circuit 30 (for example, a generator of stimulating pulses).

Figure 2:
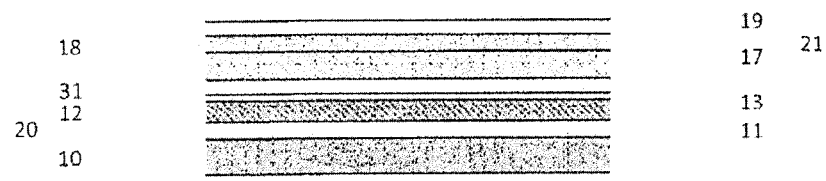
FIG. 2, a schematic cross-sectional representation of a photovoltaic device according to one alternative embodiment of the invention.

The system 200 comprises a photovoltaic device 2 of the type illustrated in FIGS. 1 and 2, made up of a photovoltaic module 22 and an LED 21, a switching system comprising two switches 24, 26 (embodied, for example, by field-effect transistors) and a control circuit 27 for controlling these switches; the control circuit 27 is powered by the module 22 (or, as a variant, by the battery 25). The control circuit may be based on a microprocessor or a dedicated analog, digital or hybrid circuit. Advantageously, the circuit measures the electrical power generated by the module and employs the result of the measurement when controlling the switches 24, 25 as will be explained below. These switches are controlled in phase opposition, i.e. when one is closed, the other is open. In particular, when the switch 24 is closed (this corresponding to the initial situation, during start-up) the current generated by the module 22 powers the LED 23, whereas when the switch 26 is closed this current recharges the battery 25 (more generally, powers an external load).

At the start of the illumination of the implanted photovoltaic module 22 using the near-infrared radiation emitted by the external source 23, said module functions in a degraded mode, because the illumination does not contain photons of sufficiently high energy to allow acceptor defects to be neutralized, but nevertheless generates enough power to power the LED 21 by way of the switch 24 (2-5 V and preferably 3 V voltage, current comprised between 5 mA and 20 mA and preferably of 15 mA, power comprised between 10 mW and 100 mW and preferably of 45 mW). Said LED then generates luminous radiation in the wavelength range absorbed by the buffer layer (typically 250 nm-400 nm and preferably about 330 nm for a buffer layer made of ZnOS). After a certain time of exposure of the photovoltaic module 22 to the photons emitted by the LED 21, the electrical performance of the photovoltaic module 22 becomes optimal. This is detected by the control circuit 27 (for example by crossing of a first preset threshold of generated electrical power), which controls open the switch 24 and controls closed the switch 26. This turns off the LED 21; charging of the secondary battery 25 may then commence. Conversely, the control circuit 27 may turn the LED 21 back on if the power generated by the module 22 drops below a second preset threshold lower than said first threshold (hysteresis). Other control logics are however envisionable, for example the use of a simple timer.

As a variant, the photovoltaic system 200 may comprise a CIGS photovoltaic module and a light-emitting diode that are not integrated into one photovoltaic device such as that in FIG. 1 or FIG. 2, but that form discrete and separate elements. These elements will then necessarily be arranged so that the light-emitting diode is able to illuminate the photovoltaic module, for example being placed facing each other. Such an embodiment may be particularly appropriate for non-implantable applications.

The invention claimed is:
1. A photovoltaic device comprising:
    a CIGS photovoltaic module having a surface, called the upper surface, intended to be exposed to luminous radiation; and
    a light-emitting diode having a luminous emission at a wavelength shorter than 600 nm, and transparent to radiation in the near infrared, fastened to said upper surface of the photovoltaic module.
2. The photovoltaic device as claimed in claim 1, in which said light-emitting diode has a luminous emission at a wavelength corresponding to a photonic energy higher than a bandgap width of a buffer layer of said photovoltaic module.
3. The photovoltaic device as claimed in claim 1, in which said CIGS photovoltaic module is suitable for generating an electrical current when its upper surface is illuminated by near infrared radiation to which said light-emitting diode is transparent.
4. The photovoltaic device as claimed in claim 1, in which said photovoltaic module comprises a plurality of photovoltaic cells connected in series.
5. The photovoltaic device as claimed in claim 4, in which said photovoltaic cells connected in series are produced in the form of a thin-film stack deposited on a common substrate.
6. The photovoltaic device as claimed in claim 1, wherein the light-emitting diode has a luminous emission at a wavelength shorter than or equal to 443 nm.

7. The photovoltaic device as claimed in claim 1, wherein the light-emitting diode has a luminous emission at a wavelength comprised between 250 and 400 nm.

8. A photovoltaic generation system comprising:
- a CIGS photovoltaic module having a surface, called the upper surface, intended to be exposed to luminous radiation; and
- a light-emitting diode having a luminous emission at a wavelength shorter than 600 nm, and transparent to radiation in the near infrared, arranged so as to be able to illuminate said photovoltaic module;
- a system of switches for selectively connecting said photovoltaic module to said light-emitting diode or to a supply terminal of an exterior load; and
- a control circuit for controlling said system of switches.

9. The photovoltaic generation system as claimed in claim 8, in which said photovoltaic module and said light-emitting diode form a photovoltaic device comprising:
- a CIGS photovoltaic module having a surface, called the upper surface, intended to be exposed to luminous radiation; and
- a light-emitting diode having a luminous emission at a wavelength shorter than 600 nm, and transparent to radiation in the near infrared, fastened to said upper surface of the photovoltaic module.

10. The photovoltaic generation system as claimed in claim 8, in which said control circuit is suitable for:
- measuring an electrical power generated by said photovoltaic module; and
- controlling said switching system depending on the measured power.

11. The photovoltaic generation system as claimed in claim 10, in which said control circuit is suitable for controlling said switching system such that said photovoltaic module powers said light-emitting diode when said measured power is below a preset threshold, then powers an exterior load connected to said supply terminal.

12. An electronic system comprising:
- a photovoltaic generation system as claimed in claim 8;
- a battery connected to said supply terminal so as to be recharged by said photovoltaic generation system; and
- at least one electronic circuit connected to said battery so as to be powered.

13. An implantable medical device comprising an electronic system as claimed in claim 12.

* * * * *